US009695121B2

(12) United States Patent
Jaegli et al.

(10) Patent No.: US 9,695,121 B2
(45) Date of Patent: Jul. 4, 2017

(54) 2,6-BIS-(AMINOMETHYL)PIPERIDINE DERIVATIVES

(71) Applicant: BASF SE, Ludwigshafen (DE)

(72) Inventors: Stephanie Jaegli, Mannheim (DE); Thomas Schmidt, Neustadt (DE); Alfred Oftring, Bad Duerkheim (DE); Alexander Panchenko, Ludwigshafen (DE); Kirsten Dahmen, Bad Duerkheim (DE); Oliver Molt, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/764,010

(22) PCT Filed: Jan. 27, 2014

(86) PCT No.: PCT/EP2014/051519
§ 371 (c)(1),
(2) Date: Jul. 28, 2015

(87) PCT Pub. No.: WO2014/118121
PCT Pub. Date: Aug. 7, 2014

(65) Prior Publication Data
US 2015/0353491 A1    Dec. 10, 2015

(30) Foreign Application Priority Data
Jan. 30, 2013   (EP) .................................... 13153262

(51) Int. Cl.
*C07D 211/26*   (2006.01)
*C07D 211/60*   (2006.01)

(52) U.S. Cl.
CPC .......... *C07D 211/26* (2013.01); *C07D 211/60* (2013.01)

(58) Field of Classification Search
None
See application file for complete search history.

(56) References Cited

U.S. PATENT DOCUMENTS

| | | |
|---|---|---|
| 5,523,467 A | 6/1996 | Okazaki et al. |
| 5,530,127 A | 6/1996 | Reif et al. |
| 6,433,042 B1 | 8/2002 | Tomotaki et al. |
| 8,524,055 B2 | 9/2013 | Fujiwara et al. |
| 2002/0058842 A1 | 5/2002 | Ansmann et al. |
| 2010/0029991 A1 | 2/2010 | Dahmen et al. |
| 2011/0124918 A1 | 5/2011 | Ernst et al. |
| 2011/0124919 A1 | 5/2011 | Ernst et al. |
| 2012/0259112 A1 | 10/2012 | Gridnev |
| 2013/0053540 A1 | 2/2013 | Luyken et al. |
| 2013/0085286 A1 | 4/2013 | Luyken et al. |
| 2014/0213697 A1 | 7/2014 | Kaffee et al. |

FOREIGN PATENT DOCUMENTS

| | | |
|---|---|---|
| DE | 26 40 408 A1 | 3/1978 |
| EP | 0 696 572 A1 | 2/1996 |
| EP | 0 963 975 A1 | 12/1999 |
| EP | 1 138 711 A1 | 10/2001 |
| EP | 1 209 146 A1 | 5/2002 |
| EP | 1 742 045 A1 | 1/2007 |
| EP | 2 626 343 A1 | 8/2013 |
| GB | 915227 A | 1/1963 |
| GB | 1 568 725 A | 6/1980 |
| JP | 60-190762 | 9/1985 |
| JP | 7-309827 | 11/1995 |
| WO | WO 99/33561 A1 | 7/1999 |
| WO | WO 99/44984 A1 | 9/1999 |
| WO | WO 2008/104553 A1 | 9/2008 |
| WO | WO 2010/009994 A2 | 1/2010 |
| WO | WO 2010/009995 A2 | 1/2010 |
| WO | WO 2011/079041 A1 | 6/2011 |
| WO | WO 2012/046781 A1 | 4/2012 |
| WO | WO 2013/030249 A1 | 3/2013 |
| WO | WO 2013/030259 A1 | 3/2013 |
| WO | WO 2014/114556 A2 | 7/2014 |

OTHER PUBLICATIONS

Chong et al., 66(23) J.O.C. 7745-7750 (2001) (CAS Abstract).*
International Search Report issued Apr. 16, 2014 in PCT/EP2014/051519.
International Preliminary Report on Patentability issued Jul. 30, 2015 in PCT/EP2014/051519.
Shigeo Nishimura, Handbook of Heterogeneous Catalytic Hydrogenation for Organic Synthesis, 2001, pp. 170-285.
V. Baliah, et al., "Synthesis of 2,6-Disubstituted Piperidines, Oxanes, and Thianes" Chemical Reviews, vol. 83, No. 4, 1983, pp. 379-423.
Office Action issued on Oct. 24, 2016 in Japanese Patent Application No. 2015-555665 (English translation only).

* cited by examiner

*Primary Examiner* — Timothy R Rozof
(74) *Attorney, Agent, or Firm* — Oblon, McClelland, Maier & Neustadt, L.L.P.

(57) ABSTRACT

The present invention relates to 2,6-bis(aminomethyl)piperidine derivatives as such (in the following text abbreviated to "2,6-BAMP derivatives") which are defined by the general formula (I) shown in the following text. In addition, the present invention relates to a process for preparing such 2,6-BAMP derivatives by hydrogenation of the corresponding 2,6-dicyanopiperidine derivatives (hereinafter abbreviated to "2,6-DCP derivatives") in the presence of a catalyst. The present invention further provides for the use of the 2,6-BAMP derivatives of the invention as hardeners for epoxy resins, as intermediate in the preparation of diisocyanates, which play an important role in the production of polyurethanes, as starters in the preparation of polyetherols and/or as monomers for polyamide production. The present invention further relates to the diisocyanates as such prepared from the 2,6-BAMP derivatives and also the corresponding preparative process.

17 Claims, No Drawings

2,6-BIS-(AMINOMETHYL)PIPERIDINE DERIVATIVES

The present invention relates to 2,6-bis(aminomethyl) piperidine derivatives as such (in the following text abbreviated to "2,6-BAMP derivatives") which are defined by the general formula (I) shown in the following text. In addition, the present invention relates to a process for preparing such 2,6-BAMP derivatives by hydrogenation of the corresponding 2,6-dicyanopiperidine derivatives (hereinafter abbreviated to "2,6-DCP derivatives") in the presence of a catalyst. The present invention further provides for the use of the 2,6-BAMP derivatives of the invention as hardeners for epoxy resins, as intermediate in the preparation of diisocyanates, which play an important role in the production of polyurethanes, as starters in the preparation of polyetherols and/or as monomers for polyamide production. The present invention further relates to the diisocyanates as such prepared from the 2,6-BAMP derivatives and also the corresponding preparative process.

It is generally known that aliphatic nitriles can be hydrogenated in the presence of hydrogen and catalysts to form the corresponding amines. Such hydrogenation processes are known both for β-amino nitriles and for various α-amino nitriles, e.g. aminoacetonitrile (AAN) or ethylenediaminediacetonitrile (EDDN), for preparing the corresponding amines such as ethylenediamine (EDA) or triethylenetetramine (TETA). Furthermore, it is known that the hydrogenation of β-amino nitriles generally proceeds without problems, while the hydrogenation of α-amino nitriles is associated with the occurrence of numerous disadvantages such as hydrogenolysis of the C—CN bond of the nitrile used or of the $H_2N$—C bond of the amine obtained by hydrogenation. The "Handbook of Heterogeneous Catalytic Hydrogenation for Organic Synthesis" (John Wiley & Sons, New York, 2001, pages 173-275) indicates the problems in the hydrogenation of α-amino nitrile for cyclic α-amino nitriles such as 1-cyclohexyl-2,5-dicyano-2,5-dimethylpyrrolidine.

WO 2008/104553 relates to a process for preparing triethylenetetramine (TETA), in which ethylenediaminediacetonitrile (EDDN) is hydrogenated in the presence of a catalyst and a solvent. Furthermore, EDDN can also be present as constituent of an amino nitrile mixture which additionally comprises ethylenediaminemonoacetonitrile (EDMN), with diethylenetriamine (DETA) being obtained from EDMN by hydrogenation. TETA and DETA are in both cases acyclic (linear) ethylene amines.

WO 2010/009995 relates to 5-isopropyl-3-aminomethyl-2-methyl-1-aminocyclohexane (carvonediamine) and a process for preparing it. Proceeding from carvone, a nitrile-comprising intermediate is formed by a multistage reaction with hydrogen cyanide and ammonia and this intermediate is in turn hydrogenated by means of hydrogen to form carvonediamine. Carvonediamine is a cyclic aliphatic (cyclohexane derivative) which is substituted by a first amino function directly on the ring and by a further amino function via a methylene bridge. In contrast to the 2,6-BAMP derivatives of the invention, carvonediamine is thus not an ethylene amine which is based on a heterocycle and has three amino functions connected via two ethylene bridges but instead is a cycloaliphatic diamine having two primary amino functions located exclusively in the substituents. Carvonediamine can be used, for example, as hardener in epoxy resins or as intermediate in the preparation of diisocyanates.

The corresponding 2,6-DCP derivatives used in the process of the invention for preparing the 2,6-BAMP derivatives are already known. Thus, for example, GB-A 915 227 describes the preparation of 2,6-dicyanopiperidine as such (in terms of the present invention, the radical $R^1$ in the formula (II) below is thus hydrogen and A, B, D are each $CH_2$), in which glutaraldehyde is reacted with hydrocyanic acid (HCN) and ammonia. However, this document does not disclose any hydrogenation of the product obtained in this process to give the corresponding aminomethyl compound. Numerous further documents which all describe processes for preparing 2,6-DCP derivatives are known in the prior art, for example CHEM. REV. 1983 (4), pages 379-423.

As indicated above in connection with WO 2010/009995, compounds having two primary amino functions ("diamines") can be used for numerous applications, for example as hardener in epoxy resins or for preparing diisocyanates. The structure of the diamine used can influence the properties of the polymer materials produced from the diamines, for example weathering resistance, hydrolysis resistance, chemicals resistance, light stability, electrical and mechanical properties. However, it can also exert an influence on the processability and the processing of the diamines to form the corresponding polymer materials, for example the curing of epoxy resins.

It is therefore an object of the present invention to provide further compounds which have two primary amino functions and also a corresponding process for preparing such compounds. The object is achieved by 2,6-bis(aminomethyl) piperidine derivatives (2,6-BAMP derivatives) of the general formula (I),

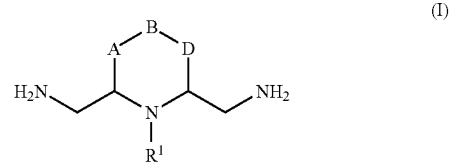

(I)

where:
A, B and D are each, independently of one another, $CH_2$, $CHR^2$ or $CR^2R^3$;
$R^1$ is hydrogen, unsubstituted or at least monosubstituted $C_1$-$C_{30}$-alkyl, unsubstituted or at least monosubstituted $C_2$-$C_{10}$-alkenyl or unsubstituted or at least monosubstituted aryl,
  where the substituents are selected from the group consisting of $C_1$-$C_4$-alkyl, aryl$^2$, —$OR^4$, —$C(O)R^6$, —$C(O)OR^4$, —O—$C(O)R^6$, —$NR^4R^5$ or halogen, and aryl$^2$ can in turn be at least monosubstituted by $C_1$-$C_4$-alkyl, —$OR^4$, —$C(O)R^6$, —$C(O)OR^4$, —O—$C(O)R^6$, —$NR^4R^5$ or halogen;
$R^2$ and $R^3$ are each, independently of one another, unsubstituted or at least monosubstituted $C_1$-$C_{10}$-alkyl or unsubstituted or at least monosubstituted aryl,
  where the substituents are selected from the group consisting of $C_1$-$C_4$-alkyl, —$OR^4$, —$C(O)R^6$, —$C(O)OR^4$, —O—$C(O)R^6$, —$NR^4R^5$ or halogen;
$R^4$ and $R^5$ are each, independently of one another, hydrogen or unsubstituted $C_1$-$C_4$-alkyl;
$R^6$ is unsubstituted $C_1$-$C_{10}$-alkyl.

The 2,6-BAMP derivatives of the invention can advantageously be prepared with a high conversion and/or high selectivity. By-products such as the corresponding monoaminomethylpiperidine derivative, which results from hydrogenolysis of one of the two C—CN bonds in the hydrogenation of the dicyano starting material, are obtained in only small amounts or can be decreased further by control of process parameters such as pressure, temperature or catalyst. Thus, for example, the ratio of N-methyl-2,6-BAMP to the corresponding monoaminomethyl by-product (N-methyl-2-aminomethylpiperidine; N-methyl-2-BAMP) can be controlled in the range from 1:1 to 15:1. In particular, the hydrogenation of 2,6-DCP to give the corresponding 2,6-BAMP as such (in the general formula (I), $R^1$ is then hydrogen) can be carried out with a high selectivity of preferably 70%, particularly preferably >85%.

Furthermore, it is advantageous that the stereoisomer ratio of the 2,6-BAMP derivatives of the general formula (I) can be regulated by adjusting the reaction conditions. If the 2,6-DCP derivatives used as starting materials are prepared from glutaric acid or glutaric acid derivatives by reaction with hydrocyanic acid and the corresponding amines, the starting materials can be provided with cis/trans ratios in the range from 80:20 to >99:1. These cis/trans ratios can be maintained in the subsequent hydrogenation to prepare the 2,6-BAMP derivatives of the invention.

Furthermore, the 2,6-BAMP derivatives of the invention can advantageously be used in the production of polymer materials such as epoxy resins, polyurethanes, polyesters, etc., in order to regulate the property profile of these polymer materials, for example in respect of weathering resistance, hydrolysis resistance, chemicals resistance, light stability, electrical and mechanical properties, and thus allow greater possible variations in the formulation of these materials.

For the purposes of the present invention, definitions such as $C_1$-$C_{30}$-alkyl, as defined above for, for example, the radical $R^1$ in formula (I), mean that this substituent (radical) is an alkyl radical having from 1 to 30 carbon atoms. The alkyl radical can be either linear or branched or optionally cyclic. Alkyl radicals which have both a cyclic component and a linear component likewise come within this definition. The same applies to other alkyl radicals such as a $C_1$-$C_4$-alkyl radical or a $C_1$-$C_{10}$-alkyl radical. Examples of alkyl radicals are methyl, ethyl, n-propyl, sec-propyl, n-butyl, sec-butyl, isobutyl, 2-ethylhexyl, tert-butyl (tert-Bu/t-Bu), pentyl, hexyl, heptyl, cyclohexyl, octyl, nonyl or decyl.

For the purposes of the present invention, definitions such as $C_2$-$C_{10}$-alkenyl, as defined above for, for example, the radical $R^1$ in formula (I), mean that this substituent (radical) is an alkenyl radical having from 2 to 10 carbon atoms. This carbon radical is preferably monounsaturated but can optionally also be doubly unsaturated or multiply unsaturated. As regards linearity, branches and cyclic constituents, what has been said above for $C_1$-$C_{30}$-alkyl radicals applies analogously. $C_2$-$C_{10}$-alkenyl is, for the purposes of the present invention, preferably vinyl, 1-allyl, 3-allyl, 2-allyl, cis- or trans-2-butenyl, ω-butenyl.

For the purposes of the present invention, the term "aryl" or the term "aryl²", as defined above for, for example, the radical $R^1$ in formula (I), means that the substituent (radical) is an aromatic. The aromatic can be a monocyclic, bicyclic or optionally polycyclic aromatic. In the case of polycyclic aromatics, individual rings can optionally be fully or partially saturated. Preferred examples of aryl are phenyl, naphthyl or anthracyl, in particular phenyl.

The present invention is described in more detail below.

The present invention firstly provides a 2,6-bis(aminomethyl)piperidine derivative (2,6-BAMP derivative) of the general formula (I),

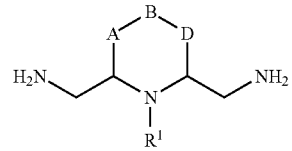

where:
A, B and D are each, independently of one another, $CH_2$, $CHR^2$ or $CR^2R^3$;
$R^1$ is hydrogen, unsubstituted or at least monosubstituted $C_1$-$C_{30}$-alkyl, unsubstituted or at least monosubstituted $C_2$-$C_{10}$-alkenyl or unsubstituted or at least monosubstituted aryl,
where the substituents are selected from the group consisting of $C_1$-$C_4$-alkyl, aryl², —OR⁴, —C(O)R⁶, —C(O)OR⁴, —O—C(O)R⁶, —NR⁴R⁵ or halogen,
and aryl² can in turn be at least monosubstituted by $C_1$-$C_4$-alkyl, —OR⁴, —C(O)R⁶, —C(O)OR⁴, —O—C(O)R⁶, —NR⁴R⁵ or halogen;
$R^2$ and $R^3$ are each, independently of one another, unsubstituted or at least monosubstituted $C_1$-$C_{10}$-alkyl or unsubstituted or at least monosubstituted aryl,
where the substituents are selected from the group consisting of $C_1$-$C_4$-alkyl, —OR⁴, —C(O)R⁶, —C(O)OR⁴, —O—C(O)R⁶, —NR⁴R⁵ or halogen;
$R^4$ and $R^5$ are each, independently of one another, hydrogen or unsubstituted $C_1$-$C_4$-alkyl;
$R^6$ is unsubstituted $C_1$-$C_{10}$-alkyl.

The 2,6-BAMP derivative is preferably defined according to the general formula (Ia),

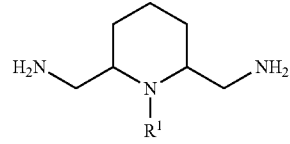

where:
$R^1$ is hydrogen, unsubstituted or at least monosubstituted $C_1$-$C_{10}$-alkyl, unsubstituted or at least monosubstituted $C_2$-$C_{10}$-alkenyl or unsubstituted or at least monosubstituted aryl,
where the substituents are selected from the group consisting of $C_1$-$C_4$-alkyl, aryl², —OR⁴, —NR⁴R⁵ or halogen,
and aryl² can in turn be at least monosubstituted by $C_1$-$C_4$-alkyl, —OR⁴, —NR⁴R⁵ or halogen;
$R^4$ and $R^5$ are each, independently of one another, hydrogen or unsubstituted $C_1$-$C_4$-alkyl.

The 2,6-BAMP derivative of the general formula (I) and even more preferably the 2,6-BAMP derivative of the general formula (Ia) is more preferably defined as follows:
$R^1$ is hydrogen, unsubstituted or at least monosubstituted $C_1$-$C_4$-alkyl and the substituent is —NR4R5;
$R^4$ and $R^5$ are each, independently of one another, hydrogen or unsubstituted $C_1$-$C_4$-alkyl;
with $R^1$ being in particular hydrogen. In the case of the general formula (Ia), this means, in this (more preferred) embodiment, that the compound in question is 2,6-BAMP as such.

In the above definition of the general formula (I) or (Ia), aryl and aryl$^2$ are preferably phenyl, naphthyl or anthracyl, in particular phenyl.

The present invention further provides a process for preparing a compound (2,6-BAMP derivative) according to the above definitions. The process of the invention can be used to prepare a single 2,6-BAMP derivative or a mixture of two or more such derivatives which come under the above-described definitions in a targeted manner. In the process of the invention, the 2,6-BAMP derivative is obtained from the corresponding 2,6-dicyanopiperidine derivative (2,6-DCP derivative) of the general formula (II) or (IIa)

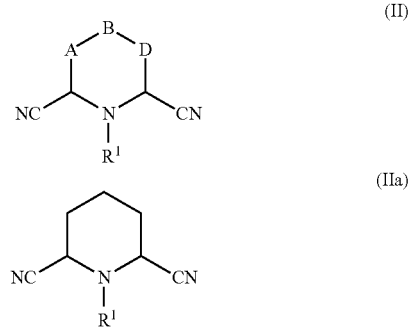

by hydrogenation in the presence of a catalyst.

The 2,6-DCP derivatives of the general formula (II) or (IIa) as such are, as indicated above, known. Compounds of this type and the associated preparative processes are described, for example, in GB-A 915 227 or CHEM. REV. 1983 (4), pages 379-423. For the sake of completeness, it will be pointed out once again that all substituents ($R^1$ to $R^6$) and variables (A, B, D) in the formula (II) always have the same meaning as described above for the corresponding 2,6-BAMP derivative of the general formula (I). The same applies analogously to the definitions/the relationship of the 2,6-DCP derivative of the general formula (IIa) to the above-described 2,6-BAMP derivative of the general formula (Ia) and also the further preferred embodiments in respect of the 2,6-BAMP derivatives of the invention indicated in the above text.

In a preferred embodiment, the 2,6-DCP derivative used for the hydrogenation is prepared by reaction of i) glutaraldehyde or a glutaraldehyde derivative with ii) hydrogen cyanide (HCN) and iii) an appropriate amine of the formula $R^1NH_2$.

For the sake of completeness, it is pointed out that in this embodiment in the case of the use of glutaraldehyde, the 2,6-DCP derivatives of the general formula (II) which are prepared are ones in which the variables A, B and D are all $CH_2$. Analogously, glutaraldehyde derivatives are used correspondingly in order to realize the further definitions ($CHR^2$ and $CR^2R^3$) for the variables A, B and D in the general formula (II) for 2,6-DCP derivatives.

The amine of the formula $R^1NH_2$ used in this embodiment is likewise known to those skilled in the art. Here, the definition of the radical $R^1$ corresponds to the definition of the radical $R^1$ in the 2,6-DCP derivatives of the general formula (II) or (IIa).

The hydrogenation to give the 2,6-BAMP derivatives of the invention is generally carried out by reacting the 2,6-DCP derivatives with hydrogen in the presence of a hydrogenation catalyst.

The hydrogenation to form the 2,6-BAMP derivative generally requires at least 4 mol of hydrogen per mol of 2,6-DCP derivative.

The temperatures at which the hydrogenation is carried out are in the range from 60 to 180° C., preferably from 80 to 140° C., in particular from 90 to 130° C.

The pressure prevailing in the hydrogenation is generally from 40 to 300 bar, preferably from 40 to 240 bar, particularly preferably from 80 to 200 bar.

In a preferred embodiment, the 2,6-DCP derivative of the formula (II) is fed to the hydrogenation at a rate which is not greater than the rate at which the 2,6-DCP derivative reacts with hydrogen in the hydrogenation.

The feed rate is preferably set so that virtually complete conversion is achieved. This is influenced by temperature, pressure, type of 2,6-DCP derivative, amount and type of the catalyst, of the reaction medium, quality of mixing of the contents of the reactor, residence time, etc.

The process of the invention is carried out in the presence of a catalyst. As catalysts, it is in principle possible to use all catalysts known to those skilled in the art for nitrile hydrogenation. It is therefore possible to use, for example, catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species as catalysts for the hydrogenation of the two nitrile functions to form the 2,6-BAMP derivative.

This includes oxidic catalysts which comprise one or more active species in the form of their oxygen-comprising compounds and skeletal catalysts (also referred to as Raney® type; hereinafter also: Raney catalyst) which are obtained by leaching (activation) of an alloy of the hydrogenation-active metal and a further component (preferably Al). The catalysts can additionally comprise one or more promoters.

In a particularly preferred embodiment, Raney catalysts, preferably Raney cobalt catalysts or Raney nickel catalysts and particularly preferably a Raney nickel catalyst which comprises at least one of the elements Ni, Cr or Fe as promoter, are used in the hydrogenation of the 2,6-DCP derivatives. The Raney cobalt catalyst is thus doped with at least one of these elements.

The catalysts can be used as all-active catalysts or in supported form. Supports used are preferably metal oxides such as $Al_2O_3$, $SiO_2$, $ZrO_2$, $TiO_2$, mixtures of metal oxides or carbon (activated carbons, carbon blacks, graphite).

Before use, the oxidic catalysts are activated outside the reactor or in the reactor by reduction of the metal oxides in a hydrogen-comprising gas stream at elevated temperature. When the catalysts are reduced outside the reactor, passivation can be effected thereafter by means of an oxygen-comprising gas stream or by embedding in an inert material in order to avoid uncontrolled oxidation in air and make safer handling possible. As inert material, it is possible to use organic solvents such as alcohols or else water or an amine, preferably the reaction product. An exception in the activation is the skeletal catalysts which can be activated by leaching with aqueous base, e.g. as described in EP-A 1 209 146. Depending on the process carried out (suspension hydrogenation, fluidized-bed process, fixed-bed hydrogenation), the catalysts are used as powder, crushed material or shaped bodies (preferably extrudates or pellets)

Particularly preferred fixed-bed catalysts are the all-active cobalt catalysts doped with Mn, P and alkali metal (Li, Na, K, Rb, Cs) which are disclosed in EP-A1 742 045. The catalytically active composition of these catalysts before reduction by means of hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, where the molar Ni:Cu ratio is greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ and $MnO_2$, respectively, and no oxygen-comprising compounds of molybdenum, for example the catalyst A which is disclosed in this document and has the composition 33% by weight of Zr, calculated as $ZrO_2$, 28% by weight of Ni, calculated as NiO, 11% by weight of Cu, calculated as CuO and 28% by weight of Co, calculated as CoO.

Further suitable catalysts are the catalysts disclosed in EP-A 696 572, whose catalytically active composition before reduction by means of hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ and $MnO_2$, respectively, for example the catalyst having the composition 31.5% by weight of $ZrO_2$, 50% by weight of NiO, 17% by weight of CuO and 1.5% by weight of $MoO_3$ which is specifically disclosed in this document. The catalysts described in WO-A-99/44984 which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight, based on (a), of a compound based on an alkali metal and/or alkaline earth metal and (d) from 0.001 to 1% by weight, based on (a), of manganese are likewise suitable.

Raney catalysts are preferably used for suspension processes. In the case of Raney catalysts, the active catalyst is produced as "metal sponge" from a binary alloy (nickel, iron, cobalt, with aluminum or silicon) by leaching out of one partner with acid or alkali. Residues of the original alloying partner often act synergistically.

The Raney catalysts used in the process of the invention are preferably produced from an alloy of cobalt or nickel, particularly preferably cobalt, and a further alloying component which is soluble in alkalis. As this soluble alloy component, preference is given to using aluminum, but it is also possible to use other components such as zinc and silicon or mixtures of such components.

To activate the Raney catalyst, the soluble alloying component is completely or partially extracted by means of alkali, for which it is possible to use, for example, aqueous sodium hydroxide solution. The catalyst can then be washed, for example with water or organic solvents.

One or more further elements can be present as promoters in the catalyst. Examples of promoters are metals of transition groups IB, VIB and/or VIII of the Periodic Table, e.g. chromium, iron, molybdenum, nickel, copper, etc.

The activation of catalysts by leaching of the soluble component (typically aluminum) can be carried out either in the reactor itself or before introduction into the reactor. The preactivated catalysts are air-sensitive and pyrophoric and are therefore generally stored and handled under a medium such as water, an organic solvent or a material which is present in the reaction according to the invention (solvent, starting material, product) or embedded in an organic compound which is solid at room temperature.

In a preferred embodiment, a Raney cobalt skeletal catalyst which has been obtained from a Co/Al alloy by leaching with aqueous alkali metal hydroxide solution, e.g. sodium hydroxide solution, and subsequent washing with water and preferably comprises at least one of the elements Fe, Ni or Cr as promoters is used according to the invention.

Such catalysts typically comprise cobalt together with 1-30% by weight of Al, in particular 2-12% by weight of Al, very particularly 3-6% by weight of Al, 0-10% by weight of Cr, in particular 0.1-7% by weight of Cr, very particularly 0.5-5% by weight of Cr, more particularly 1.5-3.5% by weight of Cr, 0-10% by weight of Fe, in particular 0.1-3% by weight of Fe, very particularly 0.2-1% by weight of Fe, and/or 0-10% by weight of Ni, in particular 0.1-7% by weight of Ni, very particularly 0.5-5% by weight of Ni, more particularly 1-4% by weight of Ni, where the weights indicated are in each case based on the total weight of the catalyst.

As catalyst in the process of the invention, a skeletal cobalt catalyst "Raney 2724" from W.R. Grace & Co., for example, can advantageously be used. This catalyst has the following composition: Al: 2-6% by weight, Co: ≥86% by weight, Fe: 0-1% by weight, Ni: 1-4% by weight, Cr: 1.5-3.5% by weight.

According to the invention, it is likewise possible to use a skeletal nickel catalyst which has been obtained from an Ni/Al alloy by leaching with aqueous alkali metal hydroxide solution, e.g. sodium hydroxide solution, and subsequent washing with water and preferably comprises at least one of the elements Fe, Cr as promoters.

Such catalysts typically comprise nickel together with 1-30% by weight of Al, in particular 2-20% by weight of Al, very particularly 5-14% by weight of Al, 0-10% by weight of Cr, in particular 0.1-7% by weight of Cr, very particularly 1-4% by weight of Cr, and/or 0-10% by weight of Fe, in particular 0.1-7% by weight of Fe, very particularly 1-4% by weight of Fe, where the weights indicated are in each case based on the total weight of the catalyst.

As catalyst in the process of the invention, a skeletal nickel catalyst A 4000 from Johnson Matthey, for example, can advantageously be used. This catalyst has the following composition:

Al: <14% by weight, Ni: ≥80% by weight, Fe: 1-4% by weight, Cr: 1-4% by weight.

In the event of decreasing activity and/or selectivity, the catalysts can optionally be regenerated by methods known to those skilled in the art, as disclosed, for example, in WO 99/33561 and the documents cited therein.

The regeneration of the catalyst can be carried out in the actual reactor (in situ) or on the catalyst removed from the reactor (ex situ). In the case of fixed-bed processes, regeneration is preferably carried out in situ, while in the case of suspension processes, preference is given to taking off part of the catalyst either continuously or discontinuously, regenerating it ex situ and returning it.

The process of the invention can be carried out in the presence of a solvent. Suitable solvents are in principle all solvents known to those skilled in the art, with the solvents preferably being inert toward the 2,6-DCP derivatives.

Possible solvents are organic solvents, for example amides such as N-methylpyrrolidone (NMP) and dimethylformamide (DMF), aromatic and aliphatic hydrocarbons such as toluene, alcohols such as methanol, ethanol, propanol, isopropanol, butanol, isobutanol, secondary butanol and tertiary butanol, amines such as EDA or ethylamines and ammonia, esters such as methyl acetate or ethyl acetate and ethers such as diisopropyl ether, diisobutyl ether, glycol dimethyl ether, diglycol dimethyl ether, dioxane and tetrahydrofuran (THF).

The solvent is preferably an amide, an aromatic hydrocarbon, an alcohol, an amine, an ester or an ether. Greater preference is given to using ethers in the process of the invention, even more preferably cyclic ethers and particularly preferably tetrahydrofuran.

The solvent is normally used in a weight ratio to the 2,6-DCP derivative used of from 0.1:1 to 15:1. The concentration of the 2,6-DCP derivative in the solution in which the hydrogenation is carried out should be selected so that a suitable feed rate or residence time can be set. The 2,6-DCP derivative is preferably mixed in an amount of from 10 to 50% by weight with the solvent. Based on the particularly preferred solvent tetrahydrofuran, it is advantageous, for example, to use the 2,6-DCP derivative in an amount of from 20 to 40% by weight, based on the solvent.

The reaction of the 2,6-DCP derivatives with hydrogen in the presence of catalysts can be carried out continuously, semicontinuously or batchwise in a fixed-bed, fluidized-bed or suspension mode in conventional reaction vessels suitable for catalysis. Reaction vessels in which contacting of the 2,6-DCP derivative and the catalyst with the hydrogen under superatmospheric pressure is possible are suitable for carrying out the hydrogenation.

The hydrogenation in the suspension mode can be carried out in a stirred reactor, jet loop reactor, jet nozzle reactor, bubble column reactor or in a cascade of identical or different reactors of this type.

The hydrogenation over a fixed-bed catalyst preferably takes place in one or more tube reactors or else shell-and-tube reactors.

The hydrogenation of the nitrile groups takes place with liberation of heat which generally has to be removed. The removal of heat can be effected by means of built-in heat exchanger surfaces, cooling jackets or external heat exchangers in a circuit to and from the reactor. The hydrogenation reactor or a hydrogenation reactor cascade can be operated in a single pass. As an alternative, a recycle mode in which part of the reactor output is recirculated to the reactor inlet, preferably without prior work-up of the recycle stream, is also possible.

In particular, the recycle stream can be cooled by means of an external heat exchanger in a simple and inexpensive way and the heat of reaction can thus be removed.

The reactor can also be operated adiabatically. In adiabatic operation of the reactor, the temperature rise in the reaction mixture can be limited by cooling of the feed streams or by introduction of "cold" organic solvent.

Since the reactor itself then does not have to be cooled, a simple and inexpensive construction is possible. An alternative is a cooled shell-and-tube reactor (only in the case of the fixed bed). A combination of the two modes of operation is also conceivable. Here, a fixed bed reactor preferably follows a suspension reactor.

The catalyst can be arranged in a fixed bed (fixed-bed mode) or be suspended in the reaction mixture (suspension mode).

In a particularly preferred embodiment, the catalyst is suspended in the reaction mixture to be hydrogenated.

The settling rate of the hydrogenation catalyst in the solvent selected should be low so that the catalyst can readily be kept in suspension.

The particle size of the catalysts used is in the case of the suspension mode therefore preferably in the range from 0.1 to 500 µm, in particular from 1 to 100 µm.

If the hydrogenation of the 2,6-DCP derivatives in the suspension mode is carried out continuously, the 2,6-DCP derivatives are preferably introduced continuously into the reactor and a stream comprising the hydrogenation products (2,6-BAMP derivatives) is taken continuously from the reactor.

In the batchwise suspension mode, the 2,6-DCP derivatives, optionally together with an organic solvent, are initially charged.

The amount of catalyst in the batchwise suspension mode is preferably from 1 to 60% by weight, particularly preferably from 5 to 40% by weight and very particularly preferably from 20 to 30% by weight, based on the total reaction mixture.

The residence time in the reactor in the batchwise suspension mode is preferably from 0.1 to 6 hours, particularly preferably from 0.5 to 2 hours.

The residence time in the reactor in the continuous suspension mode is preferably from 0.1 to 6 hours, particularly preferably from 0.5 to 2 hours.

The space velocity of the catalyst in the continuous suspension mode or in a semibatch process is from 0.1 to 5 kg, preferably from 0.1 to 2 kg, particularly preferably from 0.1 to 1 kg, of 2,6-DCP derivative per kg of catalyst and hour.

If the reaction in the suspension mode is carried out in a stirred reactor, the power input via the stirrer is preferably from 0.1 to 100 KW per $m^3$.

Used catalyst can be separated off by filtration, centrifugation or crossflow filtration. It may be necessary to compensate losses from the original amount of catalyst due to abrasion and/or deactivation by addition of fresh catalyst.

After the hydrogenation, the output from the hydrogenation can optionally be purified further. The catalyst can be separated off by methods known to those skilled in the art. After the catalyst has been separated off, the hydrogen present during the hydrogenation is generally separated off.

The removal of hydrogen is preferably effected by lowering the pressure at which the hydrogenation was carried out to a value at which hydrogen is gaseous but the other components in the reaction output are present in the liquid phase. The reaction output is preferably depressurized from a hydrogenation pressure of preferably from 60 to 325 bar, particularly preferably from 100 to 280 bar, and very particularly preferably from 170 to 240 bar, to a pressure of from 5 to 50 bar into a vessel. At the top of the vessel, hydrogen, possibly ammonia and possibly small amounts of vaporized low boilers or solvents such as THF are obtained. Hydrogen and possibly ammonia can be recirculated to the hydrogenation of the 2,6-DCP derivatives. For example, THF can be condensed out and recovered.

Organic solvents which may be present in the reaction output are likewise generally separated off by distillation. In particular, the 2,6-BAMP derivatives of the invention can be isolated from the reaction product by methods known to those skilled in the art.

The present invention additionally provides for the use of 2,6-BAMP derivatives as hardeners for epoxy resins, as intermediate in the preparation of diisocyanates, as starters in the preparation of polyetherols and/or as monomers for polyamide production.

2,6-BAMP derivatives are alternative hardeners for epoxy resins, which make new opportunities in the formulation and processing of epoxy resins possible and can be used for regulating the property spectrum of epoxy resins.

2,6-BAMP derivatives can also be used as intermediate in the preparation of the corresponding diisocyanates of the general formula (III) or formula (IIIa) shown below. In the general formulae (III) and (IIIa), the respective radicals (such as $R^1$) and variables (such as A) have the same meanings as defined above for the general formulae (I) and (Ia).

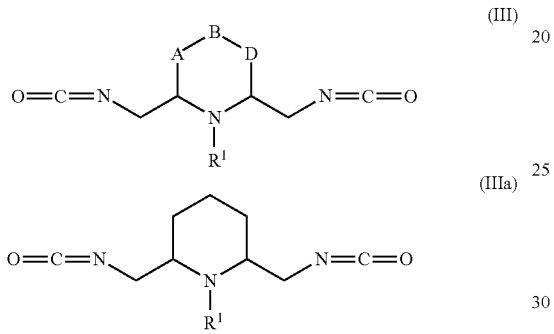

These diisocyanates are suitable for the production of light-stable polyurethanes, for example as paint/varnish or coating, and owing to their structure offer new formulation opportunities and thus access to novel, interesting property profiles. These diisocyanates can be obtained, for example, by reacting 2,6-BAMP derivatives with phosgene.

2,6-BAMP derivatives can also be used as starters in the preparation of polyetherols. 2,6-BAMP derivatives are CH-acid compounds which can be deprotonated by means of a base and can be added onto alkylene oxides such as ethylene oxide, propylene oxide and/or butylene oxide. Alkoxylated diamines can be used, for example, as catalysts in PUR production.

2,6-BAMP derivatives can be used as monomers in the production of polyamides. Thus, 2,6-BAMP derivatives can be reacted, for example, with dicarboxylic acids such as succinic acid, adipic acid, terephthalic acid and/or phthalic acid to form polymers.

The present invention therefore also provides a diisocyanate of the general formula (III),

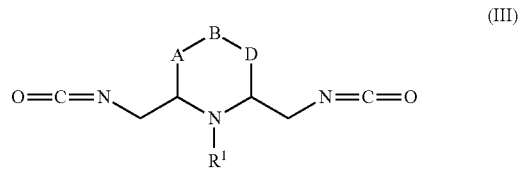

where:
$R^1$ is hydrogen, unsubstituted or at least monosubstituted $C_1$-$C_{30}$-alkyl, unsubstituted or at least monosubstituted $C_2$-$C_{10}$-alkenyl or unsubstituted or at least monosubstituted aryl, where the substituents are selected from the group consisting of $C_1$-$C_4$-alkyl, aryl$^2$, —OR$^4$, —C(O)R$^6$, —C(O)OR$^4$, —O—C(O)R$^6$, —NR$^4$R$^5$ or halogen,
and aryl$^2$ can in turn be at least monosubstituted by $C_1$-$C_4$-alkyl, —OR$^4$, —C(O)R$^6$, —C(O)OR$^4$, —O—C(O)R$^6$, —NR$^4$R$^5$ or halogen;
$R^2$ and $R^3$ are each, independently of one another, unsubstituted or at least monosubstituted $C_1$-$C_{10}$-alkyl or unsubstituted or at least monosubstituted aryl,
where the substituents are selected from the group consisting of $C_1$-$C_4$-alkyl, —OR$^4$, —C(O)R$^6$, —C(O)OR$^4$, —O—C(O)R$^6$, —NR$^4$R$^5$ or halogen;
$R^4$ and $R^5$ are each, independently of one another, hydrogen or unsubstituted $C_1$-$C_4$-alkyl;
$R^6$ is unsubstituted $C_1$-$C_{10}$-alkyl.

The diisocyanate of the general formula (III) is preferably defined by the general formula (IIIa),

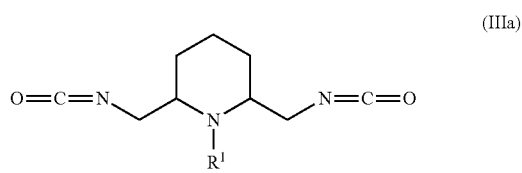

where:
$R^1$ is hydrogen, unsubstituted or at least monosubstituted $C_1$-$C_{10}$-alkyl, unsubstituted or at least monosubstituted $C_2$-$C_{10}$-alkenyl or unsubstituted or at least monosubstituted aryl,
where the substituents are selected from the group consisting of $C_1$-$C_4$-alkyl, aryl$^2$, —OR$^4$, —NR$^4$R$^5$ or halogen,
and aryl$^2$ can in turn be at least monosubstituted by $C_1$-$C_4$-alkyl, —OR$^4$, —NR$^4$R$^5$ or halogen;
$R^4$ and $R^5$ are each, independently of one another, hydrogen or unsubstituted $C_1$-$C_4$-alkyl.

Even more preferably, the following definitions are provided in the diisocyanates according to the invention having the general formula (III) or the general formula (IIIa):
$R^1$ is hydrogen, unsubstituted or at least monosubstituted $C_1$-$C_4$-alkyl and the substituent is —NR$^4$R$^5$;
$R^4$ and $R^5$ are each, independently of one another, hydrogen or unsubstituted $C_1$-$C_4$-alkyl;
with $R^1$ preferably being hydrogen.

The present invention therefore also provides a process for preparing a diisocyanate according to the above-described definitions. Processes for preparing diisocyanates from the corresponding diamines, for example by reaction with phosgene, are known to those skilled in the art, and a person skilled in the art can therefore employ these processes correspondingly.

According to the invention, the diisocyanates are preferably prepared by reacting an appropriate 2,6-BAMP derivative as per the above definitions with phosgene. Preference is given to using one 2,6-BAMP derivative, but mixtures of two or more such derivatives can optionally also be used.

The invention is illustrated below by examples.

EXAMPLE 1

Preparation of 2,6-dicyanopiperidine 62 g of water are placed in a reaction vessel and cooled to 5° C. 175.0 g of 25% strength by weight aqueous ammonia, 250.0 g of a 50% strength by weight aqueous glutaraldehyde solution and 68.3 g of hydrocyanic acid are subsequently metered in in parallel over a period of 60 minutes, with the introduction of hydrocyanic acid commencing about 10 minutes earlier. The feed streams are introduced at such a rate that a temperature of 10° C. is not exceeded. After an after-reaction time of 12 hours at not more than 10° C., the precipitate formed is filtered off with suction. 156 g of a white solid moist with water are obtained. To remove the water, the solid is taken up in 700 ml of tetrahydrofuran, dried by means of sodium sulfate and filtered. Evaporation of the filtrate on a rotary evaporator gives 109 g of a white solid which is characterized by means of 13C-NMR as 2,6-dicyanopiperidine.

EXAMPLE 2

Hydrogenation (Semibatch)

5 g of (dry) Raney cobalt and 40 g of THF were placed in a 270 ml autoclave provided with baffles and a disk stirrer. The autoclave is heated to 120° C. and pressurized with hydrogen to a total pressure of 100 bar. A mixture of 8 g of 2,6-dicyanopiperidine (prepared as described in example 1) in 72 g of THF is fed in over a period of 5.5 hours. The reaction mixture is stirred under the reaction conditions for a further 60 minutes. The hydrogenation output comprises 90% of 2,6-bis(aminomethyl)piperidine (GC-% by area). The remainder is unknown secondary components.

GC method: DB1 column, 30 m, 0.32 mm, 1 μm; 80° C. starting temperature, temperature ramp 10° C./min to 280° C.

EXAMPLE 3

Hydrogenation (Continuous)

5 g of (dry) Raney cobalt together with 40 g of THF were placed in a 270 ml autoclave provided with baffles and a disk stirrer. 15 standard l/h of hydrogen are fed in continuously. 38 g/h of a mixture of 10 g of 2,6-dicyanopiperidine (prepared as described in example 1) and 90 g of THF are pumped in continuously at 200 bar. The temperature in the reactor is 120° C. The catalyst is separated from the reactor output by continuous filtration through a sintered metal frit having a pore diameter of 500 nm. The output is depressurized via a regulating valve. In a downstream phase separator, hydrogen is subsequently separated off. A total of 114 g of 2,6-dicyanopiperidine are used.

The crude reaction mixture is firstly evaporated on a rotary evaporator and distilled at <0.5 mbar via a Vigreux column. The product goes over at 75° C. 73 g of 2,6-bis (aminomethyl)piperidine having a purity of 90-95% are obtained. The yield in the hydrogenation step is 75%, including the product content in the crude output and 60.8% of product after the distillation.

The product was characterized by GC-MS and NMR.
13C-NMR (125 MHz, THF): 60.31, 49.42, 31.4, 25.62
GC-MS: DB1 column, 30 m, 0.32 mm, 1 μm; 80° C. starting temperature, temperature ramp 10° C./min to 280° C.—retention time 9.06 min (93.3% by area).

The invention claimed is:
1. A 2,6-bis(aminomethyl)piperidine derivative (2,6-BAMP derivative) of the general formula (I),

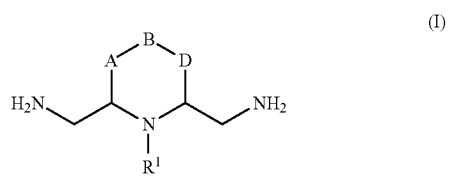

(I)

where:
A, B and D are each, independently of one another, $CH_2$, $CHR^2$ or $CR^2R^3$;
$R^1$ is unsubstituted or at least monosubstituted $C_1$-$C_{30}$-alkyl, unsubstituted or at least monosubstituted $C_2$-$C_{10}$-alkenyl or unsubstituted or at least monosubstituted aryl,
where the substituents are selected from the group consisting of $C_1$-$C_4$-alkyl, aryl$^2$, —$OR^4$, —$C(O)R^6$, —$C(O)OR^4$, —O—$C(O)R^6$, —$NR^4R^5$ or halogen,
and aryl$^2$ can in turn be at least monosubstituted by $C_1$-$C_4$-alkyl, —$OR^4$, —$C(O)R^6$, —$C(O)OR^4$, —O—C(O)$R^6$, —$NR^4R^5$ or halogen;
$R^2$ and $R^3$ are each, independently of one another, unsubstituted or at least monosubstituted $C_1$-$C_{10}$-alkyl or unsubstituted or at least monosubstituted aryl, where the substituents are selected from the group consisting of $C_1$-$C_4$-alkyl, —$OR^4$, —$C(O)OR^4$, —O—$C(O)R^6$, —$NR^4R^5$ or halogen;
$R^4$ and $R^5$ are each, independently of one another, hydrogen or unsubstituted $C_1$-$C_4$-alkyl;
$R^6$ is unsubstituted $C_1$-$C_{10}$-alkyl.

2. The 2,6-BAMP derivative according to claim 1, wherein the 2,6-BAMP derivative is defined according to the general formula (Ia),

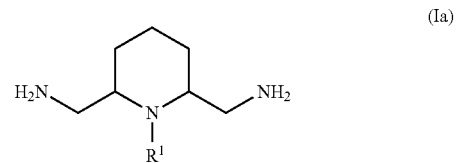

(Ia)

where:
$R^1$ is unsubstituted or at least monosubstituted $C_1$-$C_{10}$-alkyl, unsubstituted or at least monosubstituted $C_2$-$C_{10}$-alkenyl or unsubstituted or at least monosubstituted aryl, where the substituents are selected from the group consisting of $C_1$-$C_4$-alkyl, aryl$^2$, —$OR^4$, —$NR^4R^5$ or halogen, and aryl$^2$ can in turn be at least monosubstituted by $C_1$-$C_4$-alkyl, —$OR^4$, —$NR^4R^5$ or halogen; and
$R^4$ and $R^5$ are each, independently of one another, hydrogen or unsubstituted $C_1$-$C_4$-alkyl.

3. The 2,6-BAMP derivative according to claim 1, wherein:
$R^1$ is unsubstituted or at least monosubstituted $C_1$-$C_4$-alkyl and the substituent is —$NR^4R^5$; and
$R^4$ and $R^5$ are each, independently of one another, hydrogen or unsubstituted $C_1$-$C_4$-alkyl.

4. A process for preparing a 2,6-bis-aminomethyl)piperidine derivative, a 2,6-BAMP-derivative, according to the general formula (I)

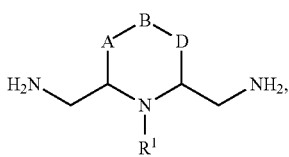

wherein the 2,6-BAIMP-derivative is obtained from the corresponding 2,6-dicyanopiperidine derivative, the 2,6-DCP-derivative, of the general formula (II) or (IIa)

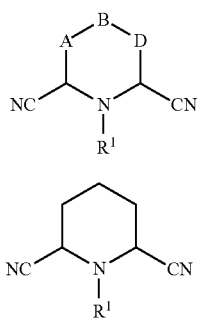

by hydrogenation in the presence of a catalyst,
wherein

A, B and D are each, independently of one another, $CH_2$, $CHR^2$ or $CR^2R^3$;

$R^1$ is unsubstituted or at least monosubstituted $C^1C^{30}$-alkyl, unsubstituted or at least monosubstituted $C_2$-$C_{10}$-alkenyl or unsubstituted or at least monosubstituted aryl, where the substituents are selected from the group consisting of $C_1$-$C_4$-alkyl, $aryl^2$, —$OR^4$, —$C(O)R^6$, —$C(O)OR^4$, —O—$C(O)R^6$, —$NR^4R^5$ or halogen, and $aryl^2$ can in turn be at least monosubstituted by $C_1$-$C_4$alkyl, —$OR^4$, —$C(O)R^6$, —$C(O)R^4$, —O—$C(O)R^6$, —$NR^4R^5$ or halogen;

$R^2$ and $R^3$ are each, independently of one another, unsubstituted or at least monosubstituted $C_1$-$C_{10}$-alkyl or unsubstituted or at least monosubstituted aryl, where the substituents are selected from the group consisting of $C_1$-$C_4$-alkyl, —$OR^4$—$C(O)R^6$, —$C(O)OR^4$, —O—$C(O)R^6$, —$NR^4R^5$ or halogen;

$R^4$ and $R^5$ are each, independently of one another, hydrogen or unsubstituted $C_1$-$C_4$-alkyl; and $R^6$ is unsubstituted $C_1$-$C_{10}$-alkyl.

5. The process according to claim 4, wherein a Raney catalyst, preferably a Raney nickel catalyst or a Raney cobalt catalyst, in particular a Raney cobalt catalyst, which comprises at least one of the elements Fe, Ni or Cr as promoter is used as catalyst.

6. The process according to claim 4, wherein the hydrogenation is carried out in a solvent which is an amide, an aromatic hydrocarbon, an alcohol, an amine, an ester or an ether.

7. The process according to claim 4, wherein the hydrogenation is carried out at a pressure from 80 to 200 bar or at a temperature from 90 to 130° C.

8. The process according to claim 4, wherein the 2,6-DCP derivative used for the hydrogenation is prepared by reaction of i) glutaraldehyde or a glutaraldehyde derivative with ii) hydrogen cyanide (HCN) and iii) an appropriate amine of the formula $R^1NH_2$.

9. A method comprising a step, wherein a 2,6-BAMP derivative according to the definition of the general formula (I) in claim 4 is employed as hardener for epoxy resins.

10. A diisocyanate of the general formula (III),

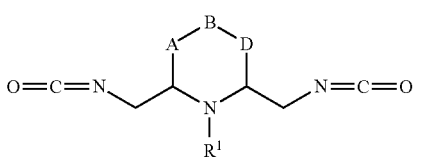

where:

A, B and D are each, independently of one another, $CH_2$, $CHR^2$ or $CR^2R^3$;

$R^1$ is hydrogen, unsubstituted or at least monosubstituted $C_1$-$C_{30}$-alkyl, unsubstituted or at least monosubstituted $C_2$-$C_{10}$-alkenyl or unsubstituted or at least monosubstituted aryl, where the substituents are selected from the group consisting of $C_1$-$C_4$-alkyl,$aryl^2$, —$OR^4$, —$C(O)R^6$, —$C(O)OR^4$, —O—$C(O)R^6$, —$NR^4R^5$ or halogen, and $aryl^2$ can in turn be at least monosubstituted by $C_1$-$C_4$-alkyl, —$OR^4$, —$C(O)R^6$, —$C(O)OR^4$, —O—$C(O)R^6$, —$NR^4R^5$ or halogen;

$R^2$ and $R^3$ are each, independently of one another, unsubstituted or at least monosubstituted $C_1$-$C_{10}$-alkyl or unsubstituted or at least monosubstituted aryl, where the substituents are selected from the group consisting of $C_1$-$C_4$ alkyl, —$OR^4$—$C(O)R^6$, —$C(O)OR^4$, —O—$C(O)R^6$, —$NR^4R^5$ or halogen;

$R^4$ and $R^5$ are each, independently of one another, hydrogen or unsubstituted $C_1$-$C_4$-alkyl; and $R^6$ is unsubstituted $C_1$-$C_{10}$-alkyl.

11. The diisocyanate according to claim 10, wherein the diisocyanate is defined according to the general formula (IIIa),

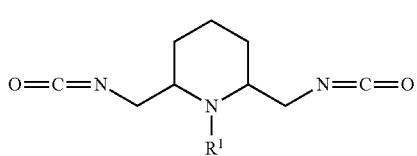

where:

$R^1$ is hydrogen, unsubstituted or at least monosubstituted $C_1$-$C_{10}$-alkyl or unsubstituted or at least monosubstituted aryl, where the substituents are selected from the group consisting of $C_1$-$C_4$-alkyl, $aryl^2$, —$OR^4$, —$NR^4R^5$ or halogen, and $aryl^2$ can in turn be at least monosubstituted by $C_1$-$C_4$-alkyl, —$OR^4$, —$NR^4R^5$ or halogen;

$R^4$ and $R^5$ are each, independently of one another, hydrogen or unsubstituted $C_1$-$C_4$-alkyl.

12. A process for preparing a diisocyanate according to claim 10, wherein a 2,6-BAMP derivative according to the definition of the general formula (II) in claim 4 is reacted with phosgene.

13. A method comprising a step, wherein a 2,6-BAMP derivative according to the definition of the general formula (I) in claim 4 is employed as intermediate in the preparation of diisocyanates.

14. A method comprising a step, wherein a 2,6-BAMP derivative according to the definition of the general formula (I) in claim 4 is employed as starter in the preparation of polyetherol or as monomer for polyamide production.

15. The process according to claim 4, wherein the hydrogenation is carried out at a pressure from 80 to 200 bar and at a temperature from 90 to 130° C.

16. The process according to claim 4, wherein the catalyst is a Raney nickel catalyst or a Raney cobalt catalyst.

17. The process according to claim 6, wherein the solvent is tetrahydrofiiran.

* * * * *